United States Patent
Sirokman

(10) Patent No.: US 7,798,974 B2
(45) Date of Patent: Sep. 21, 2010

(54) AUTOMATED PROVISION OF INFORMATION RELATED TO AIR EVACUATION FROM A CHEST CAVITY

(75) Inventor: William A. Sirokman, Kirkland, WA (US)

(73) Assignee: Spiration, Inc., Redmond, WA (US)

(*) Notice: Subject to any disclaimer, the term of this patent is extended or adjusted under 35 U.S.C. 154(b) by 669 days.

(21) Appl. No.: 11/738,412

(22) Filed: Apr. 20, 2007

(65) Prior Publication Data

US 2007/0250022 A1    Oct. 25, 2007

Related U.S. Application Data

(62) Division of application No. 10/259,007, filed on Sep. 26, 2002, now Pat. No. 7,207,946.

(60) Provisional application No. 60/379,431, filed on May 9, 2002.

(51) Int. Cl.
*A61B 5/08* (2006.01)
(52) U.S. Cl. .................. 600/529; 600/542; 600/538
(58) Field of Classification Search .......... 600/529–543, 600/300, 301
See application file for complete search history.

(56) References Cited

U.S. PATENT DOCUMENTS

| | | | |
|---|---|---|---|
| 3,683,913 A | 8/1972 | Kurtz et al. | |
| 4,301,810 A | 11/1981 | Belman | |
| 4,569,674 A | 2/1986 | Phillips et al. | |
| 4,592,741 A | 6/1986 | Vincent | |
| 4,654,029 A | 3/1987 | D'Antonio | |
| 4,685,908 A | 8/1987 | Kurtz | |
| 4,745,925 A | 5/1988 | Dietz | |
| 5,300,050 A | 4/1994 | Everett, Jr. et al. | |
| 5,421,325 A * | 6/1995 | Cinberg et al. | 128/200.26 |

(Continued)

FOREIGN PATENT DOCUMENTS

EP    0 743 071    11/1996

(Continued)

OTHER PUBLICATIONS

Marco: Bubble Detector, from webmaster@marco.de, from Website on Mar. 21, 2002; pp. 1-3.

(Continued)

*Primary Examiner*—Charles A Marmor, II
*Assistant Examiner*—Navin Natnithithadha
(74) *Attorney, Agent, or Firm*—Knobbe, Martens, Olson & Bear LLP

(57) ABSTRACT

A device according to an aspect of the invention includes an air escapement conduit having an inlet port providing air communication with a chest cavity and an outlet port providing air communication with a vacuum source, the conduit allowing an air flow from the inlet port to the outlet port in response to a pressure differential between the ports, and a detector responsive to the air flow that provides a signal related to the air flow. The device may include an indicator device operable to provide evacuation information in response to the signal. The air escapement conduit may include a bubble chamber or a valving mechanism. The detector may be a pressure differential sensor operable to detect a difference in air pressure between the inlet port and the outlet port, and generate a signal related to the difference.

19 Claims, 3 Drawing Sheets

U.S. PATENT DOCUMENTS

| | | | |
|---|---|---|---|
| RE35,225 | E | 4/1996 | Herweck et al. |
| 5,989,234 | A | 11/1999 | Valerio et al. |
| 6,338,728 | B1 | 1/2002 | Valerio et al. |
| 6,544,192 | B2 | 4/2003 | Starr et al. |
| 6,849,049 | B2 * | 2/2005 | Starr et al. ............... 600/538 |
| 7,207,946 | B2 | 4/2007 | Sirokman |
| 2002/0029004 | A1 * | 3/2002 | Starr et al. ............... 600/538 |
| 2003/0212337 | A1 * | 11/2003 | Sirokman ............... 600/529 |

FOREIGN PATENT DOCUMENTS

| | | |
|---|---|---|
| GB | 2 082 071 | 3/1982 |

OTHER PUBLICATIONS

EDO Certamics Products and Services, from webmaster@edocorp.com; from website on Mar. 21, 2002; pp. 1,2.

SIII Control and Display Modules; from webmaster@stoeckert.de; from website on Mar. 21, 2002; pp. 15.

Chest Drains, from webmaster@surgical-tutor.org.uk; from Website on Mar. 21, 2002; pp. 1-3.

Tube Thorascostomy; from webmaster@merck.com/pubs/mmanual; from Website Mar. 21, 2003, pp. 1, 2.

Exploring Chest Drain Options; from webmaster google.com; RNWeb: Continuing Education; from website on Mar. 21, 2002; pp. 1-6.

Chest Drains, from webmaster@atroi.ed/cp., from website Mar. 21, 2002; pp. 1-3.

Oasis Dry Suction Chest Drains; Instructions for Use; Atrium Medical Corporation, Hudson New Hampshire, on Mar. 27, 2002,pp. 1-4.

Understanding Chest Drainage; from webmaster@nursingceu.com; from website on Mar. 21, 2002; pp. 1-15.

* cited by examiner

AUTOMATED PROVISION OF INFORMATION RELATED TO AIR EVACUATION FROM A CHEST CAVITY

PRIORITY

This application is a divisional application of U.S. application Ser. No. 10/259,007, filed on Sep. 26, 2002, which claims priority benefit to U.S. provisional application No. 60/379,431, filed on May 9, 2002

FIELD OF THE INVENTION

The present invention is generally directed to a device, system, and method providing an automated air evacuation indicator for use in draining air and fluid from a chest cavity. The present invention is more particularly directed to automatically providing visual, auditory, and digital information related to air being evacuated from a patient's chest cavity.

BACKGROUND

The primary function of the lungs is breathing and gas exchange. Air is primarily taken into the lungs during inhalation by contraction of the diaphragm, and also by upward and outward movement of the ribs, and outward movement of the sternum. The size of the chest cavity increases, allowing the lungs to expand. When inhalation is complete, the central nervous system signals the respiratory center in the brain that enough air has entered the lungs and exhalation occurs. During exhalation, the diaphragm relaxes and the ribs move down and in, lessening the size of the chest cavity. As the lungs are "squeezed," volume is reduced. The diaphragm returns to its original position. Negative pressure is always present within the pleural or chest space and creates a vacuum or suction called intrapleural pressure. This vacuum keeps the lungs against the chest wall, preventing lung collapse even during forced exhalation. Intrapleural pressure is always slightly negative compared to atmospheric pressure. When this intrapleural pressure is lost or disrupted, the lung collapses.

Lung tissue is a very delicate organ and structure. Any penetration of the pleura or the lung parenchyma typically results in air leakage (pneumothorax) and bleeding (hemothorax). When the lung is damaged and leaks air, the lung collapses because of the loss of vacuum in the chest cavity, and because accumulation of air in the thorax cavity mechanically compresses the lung. If there is only a minimal amount of air accumulated, it can be reabsorbed. This is commonly the case with small blunt trauma, in which the lung ruptures and then heals itself quickly. When more than a minimal amount of air has accumulated, or when a persistent or continuous leakage of air either out of the lungs or into the chest cavity from an external opening exists, the pneumothorax is generally resolved by the placement of chest tubes connected to a vacuum drain system or a valve. When a severe penetrating thoracic trauma occurs and severe pneumothorax and hemothorax are observed, surgical tissue repair may be indicated. Unresolved and untreated large pneumothorax could be fatal Disruption of the sealed pleural and thoracic space always occurs during thoracic surgery. Prolonged and extensive air leaks are frequently observed after thoracic surgery that involves resection of diseased lung tissue. In addition, disruption can also be produced by trauma, lung surgery or surgery of adjacent organs with inadvertent lung tissue perforation. Occasionally, spontaneous pneumothorax is observed in patients with severely diseased tissue after chest trauma or a cough. Even without disruption of the pleural and thoracic space, post-operative care after surgery involving the heart or other organs near the plural cavity usually includes placement of chest tubes and application of a vacuum drain to evacuate air and re-establish the negative pressure to ensure lung expansion.

For many years, the standard apparatus for draining the pleural or chest cavity was a vacuum drainage system known as the "3-bottle set-up" which includes a collection bottle, a water-seal bottle, and a suction-control bottle. The three bottles are connected in series by various tubes to apply suction to the pleural cavity to withdraw liquid and air, and discharge the fluid into the collection bottle. A chest tube runs from the patient's pleural cavity to the collection bottle, and the suction bottle is connected by a tube to a suction source. Air withdrawn from the chest cavity first enters the collection bottle, and then passes into the water-seal bottle, where it bubbles through water in the water-seal bottle. The water in the water seal also acts as a one-way valve preventing back flow of air into the chest cavity, and as an escapement mechanism for evacuation air flow. The suction level is regulated by filling the suction-control bottle with water to a desired level. Suction pressure or vacuum is usually provided by a central vacuum supply in a hospital to permit withdrawal of fluids such as blood, water and air from a patient's pleural cavity. The suction establishes a pressure differential between the suction source and the internal pressure in the patient's chest. This system is sometimes known as an "underwater" or "wet" system because water is used in the suction-control chamber.

Various inefficiencies existed in the 3-bottle set-up resulting from the many separate components, the large number of connections, and complications in its use. About 30 years ago, the 3-bottle set-up lost favor with the introduction of an underwater-seal drainage system that employed a single, preformed, self-contained unit that embodies the 3-bottle techniques with three separate chambers performing the same functions. The desired suction level is established by the water level in the suction-control chamber. The single, preformed unit is easily portable and is disposable.

"Dry" or "waterless" chest drain systems were developed to address the perceived shortcomings of the "wet" or "underwater" systems. The dry systems follow the same fundamental principles of the wet systems including the water-seal chamber, but use a plurality of valves to control suction pressure instead of a wet suction chamber.

An important aspect of treating a patient with a pneumothorax is to know the status of any air leak. This includes the rate of air being leaked into the chest cavity and when it leaked. It is also important to know whether air is entering into the chest drain system from a source other than the patient, such as a system leak. This information is obtained by observing bubbles in the water-seal chamber presently used by both the current underwater and waterless chest drain systems. As the vacuum draws air and liquid from the chest cavity, air from the chest cavity flows through the water seal and creates bubbles. To determine the rate at which air is being evacuated from the patient, an observer must observe and estimate the number of bubbles created in the water seal. If the observer sees continuous bubbling, a persistent air leak exists. If the observer sees intermittent bubbling, an intermittent leak exists, and no bubbling indicates no air leak exists. Graduated air leak monitors have been incorporated into chest drain systems to assist the observer in monitoring and quantifying patient air leak trends. However, no present apparatus or method exists for determining the rate at which air is being evacuated from a patient without a person actually observing the water-seal portion of the chest drain system.

Furthermore, no present apparatus exists for providing a history of the patient's air evacuation, sounding an alarm if the air evacuation rises above a predetermined level, or if the chest drain becomes occluded or fails.

Furthermore, patients frequently have intermittent air leaks that may be missed or misinterpreted if the observer was not present when they occurred. Because of unrecognized intermittent air leaks, many patients require re-placement of chest tubes after the tubes were removed, creating increased morbidity and cost. Therefore, the present system of chest tube monitoring does not adequately provide a continuous monitoring system. Another unrecognized complication is the chest tube becoming plugged or accidentally kinked, impairing its function and causing an observer to assume that the air leak has stopped because no bubbles are observed.

In view of the foregoing, there is a need in the art for a new and improved apparatus and method for improving the monitoring of evacuation of air by a chest drain without the need for constant visual observation of the bubbles. There is also a need for providing trending information, and for providing an alarm when excessive air leaks occur or when air evacuation suddenly stops. The present invention is directed to a device, system, and method that provide such an improved apparatus and method for monitoring chest air evacuation.

SUMMARY

The present invention provides a device providing a signal for indicating information related to air evacuation from a chest cavity. The device includes an air escapement conduit having an inlet port that provides air communication with the chest cavity and an outlet port that provides air communication with a vacuum source, the conduit allowing an air flow from the inlet port to the outlet port in response to a pressure differential between the ports. The device also includes a detector responsive to the air flow that provides a signal related to the air flow. The air escapement conduit may include a bubble chamber having a fluid disposed between the inlet port and the outlet port, the bubble chamber arranged so that air flowing between the inlet port and the outlet port flows through the fluid and forms bubbles. The air escapement conduit may include a valving mechanism. The detector may be a pressure differential sensor operable to detect a difference in air pressure between the inlet port and the outlet port, and generate a signal related to the difference. The detector may be a bubble counter operable to count bubbles in the fluid and generate a signal related to counted bubbles, and the detector is further configured for connection to an indicator device operable to indicate air evacuation from the chest cavity in response to the bubble detection signal.

The invention additionally provides a device providing a signal for indicating information related to air evacuation from a chest cavity. The device includes an air escapement conduit having an inlet port providing air communication with the chest cavity and an outlet port providing air communication with a vacuum source, the conduit allows an air flow from the inlet port to the outlet port in response to a pressure differential between the ports, and an air pressure detector responsive to air pressures at the inlet and outlet ports, and that provides a signal having features related to the air pressures. The air pressure detector may be further responsive to ambient air pressure and provide a signal having features related to the ambient air pressure.

The invention further provides a device providing a signal for indicating information related to air evacuation from a chest cavity. The device including a bubble chamber having an inlet port provides air communication with the chest cavity, an outlet port provides air communication with a vacuum source, and a fluid, the bubble chamber arranged so that an air flow between the inlet port and the outlet port flows through the fluid and forms bubbles. The device further includes a detector responsive to the air flow that provides a signal related to the air flow. The detector may be a pressure differential sensor operable to detect a difference in air pressure between the inlet port and the outlet port, and generate a signal related to the difference. The detector may be a bubble counter operable to count bubbles in the fluid and generate a signal related to counted bubbles, and the detector is further configured for connection to an indicator device operable to indicate air evacuation from the chest cavity in response to the bubble detection signal. The signal may include information related to air volume evacuated from the chest cavity, to negative air evacuation pressure applied to the chest cavity, or to respiration rate of the chest cavity.

The invention still further provides a device providing a signal for indicating information related to air evacuation from a chest cavity. The device includes a valving mechanism having an inlet port providing air communication with the chest cavity and an outlet port providing air communication with a vacuum source, the valving mechanism allowing an air flow from the inlet port to the outlet port in response to a pressure differential between the ports. The device further includes a detector responsive to the air flow that provides a signal related to the air flow. The detector may be further operable to detect an allowance of the air flow by the valving mechanism, and the signal generated is related to the allowance. The detector may further include a pressure differential sensor operable to detect a difference in air pressure between the inlet port and the outlet port, and the signal generated is related to the pressure differential. The signal may include information related to air volume evacuated from the chest cavity, to negative air evacuation pressure applied to the chest cavity, or to respiration rate of the chest cavity.

The invention also provides an air evacuation indicator for providing information about air evacuation from a chest cavity. The indicator includes an air escapement conduit having an inlet port providing air communication with the chest cavity and an outlet port that provides air communication with a vacuum source, the conduit allowing an air flow from the inlet port to the outlet port in response to a pressure differential between the ports. The indicator also includes a detector responsive to the air flow that provides a signal related to the air flow, and an indicator device operable to provide evacuation information in response to the signal. The detector may be an air pressure detector responsive to air pressures at the inlet and outlet ports, and that provides a signal having features related to the air pressures. The air pressure detector may be further responsive to ambient air pressure and that provides a signal having features related to the ambient air pressure. The air escapement conduit may include a bubble chamber having a fluid disposed between the inlet port and the outlet port, the bubble chamber arranged so that air flowing between the inlet port and the outlet port flows through the fluid and forms bubbles. The detector may be a bubble counter operable to count bubbles in the fluid and generate a signal related to counted bubbles. The air escapement conduit may include a mechanical valving mechanism. The detector may be a pressure differential sensor operable to detect a difference in air pressure between the inlet port and the outlet port, and generate a signal related to the difference. The indicator device may be further operable to correlate time of occurrence with signal features, to discriminate features of the signal to produce separate corresponding indications, and to provide an alarm when a volume of air evacuated in a selected unit of time exceeds a predetermined level. The evacuation information may include air volume evacuated from the chest cavity, air volume evacuated per selected unit of time over time, rate of air volume evacuation from the chest cavity, negative air evacuation pressure applied to the chest cavity, or to respiration rate of the chest cavity. The rate of air volume evacuated may be indicated in bubbles evacuated over a unit of time. The indicator device may include an audio element, a digital indicator device, a storage device arranged to store data representative of the signal, or an optical indicator element, which may be a light emitting diode.

The invention still further provides a method of providing a signal indicating information related to air evacuation from a chest cavity. The method includes the steps of inserting an air escapement conduit into an air evacuation pathway between the chest cavity and a vacuum source, the air escapement conduit allowing an air flow in response to a pressure differential between the ports, and generating a signal related to the air flow.

The invention also provides a method of providing a signal indicating information related to air evacuation from a chest cavity. The method includes the steps of inserting an air escapement conduit into an air evacuation pathway between the chest cavity and a vacuum source, the air escapement conduit allowing an air flow in response to a pressure differential between the ports, generating a signal related to the air flow, and indicating air evacuation information in response to the signal. The air escapement conduit may include a bubble chamber having a fluid disposed between the inlet port and the outlet port, the bubble chamber arranged so that air flowing between the inlet port and the outlet port flows through the fluid and forms bubbles. The step of generating a signal may include the further step of counting bubbles in the fluid and generating a bubble detection signal related to counted bubbles. The air escapement conduit may include a mechanical valving mechanism. The step of generating a signal may include the further step of detecting a difference in air pressure between the inlet port and the outlet port, and generating a signal related to the difference. The step of indicating may further include a flash of light, and the flash of light may be provided by a light emitting diode. The step of indicating may include a sound, a representation of air evacuated as volume per selected unit of time, and providing an alarm when the air evacuated per selected unit of time exceeds a predetermined level. The method may further include the additional step of storing data representative of the signal.

The invention still further provides device providing a signal for indicating information related to air evacuation from a chest cavity. The device including means for allowing an air flow in an air escapement pathway between the chest cavity and a vacuum source in response to a pressure differential between the ports, and means for generating a signal related to the air flow.

The invention yet still further provides a device indicating information related to air evacuation from a chest cavity. The device including means for allowing an air flow in an air escapement pathway between the chest cavity and a vacuum source in response to a pressure differential between the ports, means for generating a signal related to the air flow, and means for indicating air evacuation information in response to the signal.

These and various other features as well as advantages which characterize the present invention will be apparent from a reading of the following detailed description and a review of the associated drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

DETAILED DESCRIPTION

Figure 1:
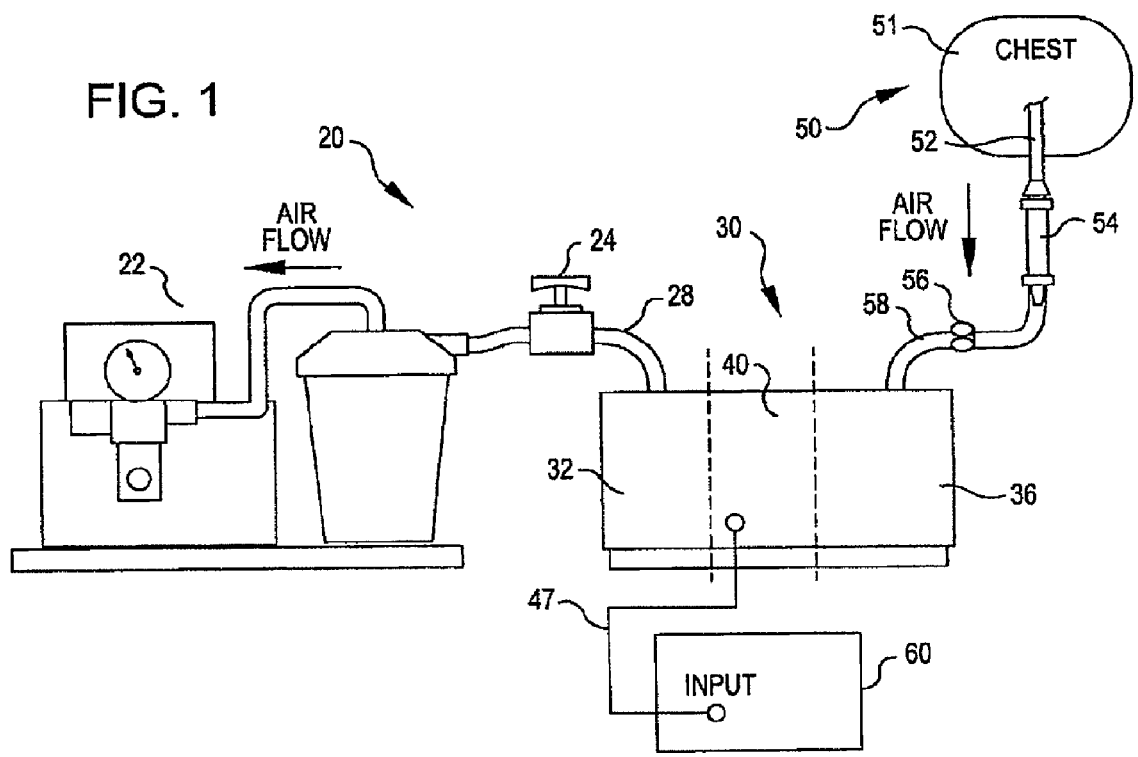
FIG. 1 illustrates an automated chest air evacuation detector for an underwater chest drain system, according to an embodiment of the invention.

In the following detailed description of exemplary embodiments of the invention, reference is made to the accompanying drawings that form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined only by the appended claims.

Additionally, throughout the specification, claims, and drawings, the term "air evacuation" means withdrawing air from a plural space (pneumothorax), where the pneumothorax is from any source. The pneumothorax may be of any type, including closed, open, and traumatic.

Throughout the specification and claims, the following terms take the meanings explicitly associated herein unless the context clearly dictates otherwise. The term "circuit" means one or more passive and/or active components that are arranged to cooperate with one another to provide a desired function. The term "signal" means at least one current signal, voltage signal or data signal. The meaning of "a", "an", and "the" include plural references. The meaning of "in" includes "in" and "on." Referring to the drawings, like numbers indicated like parts throughout the views. Additionally, a reference to the singular includes a reference to the plural unless otherwise stated or inconsistent with the disclosure herein.

FIG. 1 illustrates an automated chest air evacuation detector for an underwater chest drain system, according to an embodiment of the invention. Automated chest drain system 20 includes a suction machine or vacuum source 22, a self-contained underwater chest drain unit 30, and an air evacuation indicator 60, all providing chest drainage to patient 50 and an automatic indication of air evacuation. The self-contained, underwater chest drain unit 30 includes a collection chamber 36, an air escapement conduit in the form of a water-seal chamber 40, and a manometer chamber (or regulator) 32. The patient side of system 20 includes chest drain tube 52, chest drain valve 54, inlet clamp 56, and inlet tube 58. Vacuum source 22 portion includes a vacuum line 28 and a vacuum inlet control valve 24. A description of the air evacuation indicator 60 begins in conjunction with FIG. 2.

Chest drain tube 52 is surgically placed into the patient's chest cavity 51 to drain air, liquid, and blood (hereafter collectively referred to as "fluid") from the chest cavity 51 of a patient 50. The drainage may be indicated to evacuate a pneumothorax in the chest cavity 51 due to any reason. Inlet tube 58 is coupled to the chest drain unit 30. Vacuum source 22 is connected in series through chambers 32, 40, and 36, and then to the patient's chest cavity 51. Chest drain valve 54 is a one-way valve allowing fluid to be withdrawn from chest cavity 51, but prevents fluid from entering. Use of chest drain valve 54 is optional, and may be disposed between chest drain tube 52 and inlet tube 58. Inlet clamp 56 is used to isolate chest cavity 51 from underwater chest drain unit 30, typically when connecting or disconnecting underwater chest drain unit 30. Collection chamber portion 36 is arranged to collect liquids withdrawn from the chest cavity 51. When the air escapement conduit is embodied as a water-seal chamber 40, it typically contains a "U"-shaped column filled with water to form an air seal and one-way valve. Air evacuated from the chest cavity 51 flows through the water and forms bubbles. Manometer chamber portion 32, also known as suction-control chamber, regulates the vacuum applied to the chest cavity 52. Vacuum line 28 connects vacuum source 20 to the self-contained, underwater chest drain unit 30, and vacuum inlet valve 24 when turned off isolates vacuum source 20. Air evacuation indicator 60 indicates information about the number of bubbles formed in water-seal chamber 40 by air drawn into the underwater chest drain system 22 from the patient's chest cavity 51. An alternative embodiment of chest drain system 20 eliminates the vacuum source 20 and vents to the atmosphere.

Figure 2:
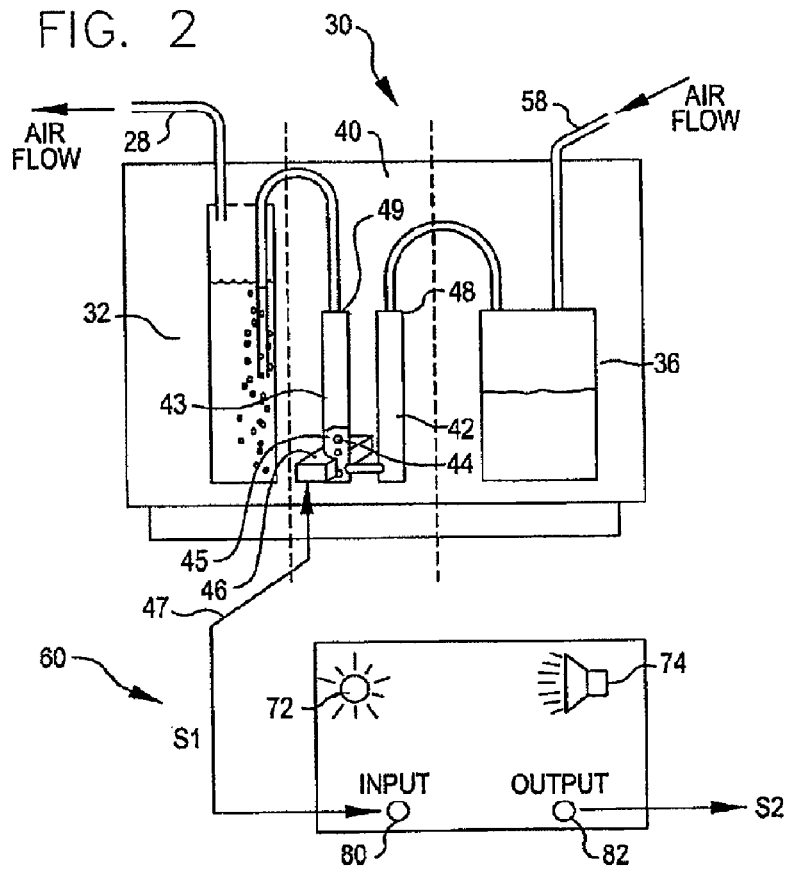
FIG. 2 illustrates additional elements of self-contained underwater chest drain system and indicator panel, according to an embodiment of the invention.

FIG. 2 illustrates additional elements of self-contained underwater chest drain unit 30 and air evacuation indicator 60, according to an embodiment of the invention. Collection chamber portion 36 includes a chamber that collects liquid drained from the patient. Manometer chamber portion 32 includes a chamber filled with water to various levels by a health care provider, the water level in the chamber regulating the vacuum applied to the patient's chest cavity 51 by underwater chest drain unit 30. Water-seal chamber 40 includes a water-seal "U"-shaped column referred to as bubble chamber 42, a water-seal chamber portion inlet port 48, a water-seal chamber portion outlet port 49, and a bubble detector 46. Air evacuation indicator 60 includes an input jack 81 for receiving air flow signal S1, an indicator signal (S2) output jack 82, an optical indicator device 72, and an audio indicator device 74. Air evacuation indicator 60 may be coupled to drain unit 30 by detector coupler 47.

Bubble chamber 42 typically is a "U"- or "J"-shaped, sealed chamber open only at inlet port 48 and outlet port 49, filled with a fluid 45 that is typically water, and forms an air seal and one-way valve between the patient 50 and the vacuum source 22. Bubble chamber 42 is arranged to form an escapement mechanism whereby air evacuated from the patient's chest cavity 51 by vacuum source 22 flows through the fluid 45 in bubble chamber 42 and creates discrete bubbles 44 (reference number 44 is used to refer to an individual bubble and a plurality of bubbles, as dictated by the context). Bubble chamber 42 includes a fluid 45 such as water contained in a fluid column 43, the fluid column 43 being dimensioned and disposed so that the bubbles 44 pass in single file for counting.

Bubble detector 46 is a detector operable to detect individual bubbles 44 flowing in the fluid column 43 of bubble chamber 42, and to generate the air flow signal S1. Signal S1 includes features related to the air evacuated from the chest cavity 51. The features of signal S1 may include information related to bubbles detected, a pressure differential across the bubble chamber 42, pressures in portions of bubble chamber 42, and ambient air pressure. For the embodiment illustrated in FIG. 2, signal S1 includes features related to individual bubbles detected or counted by bubble detector 46. The size and frequency of the bubbles are related to the volume and rate of air evacuation from chest cavity 51.

FIG. 2 illustrates the bubble detector 46 detecting a bubble 44 rising vertically in the fluid column 43 of bubble chamber 42. In an alternative embodiment, bubble detector 46 may be located to detect a bubble 44 moving horizontally in a horizontal portion of the fluid column 43, for example by locating the detector at the bottom of a "U"-shaped bubble chamber 42. Bubble detector 46 may be physically located at any place along the pathway followed by bubbles 44 in bubble chamber 42. Bubble detector 46 may be any device known to those in the art operable to detect bubbles 44 and generate the air flow signal S1 based on bubbles detected, including optical or ultrasonic detectors. Signal S1 may be provided by the bubble detector 46 at a jack (not shown) or by detector coupler 47, which may be a wire conductor for connection to an indicator device, such as air evacuation indicator 60. In an alternative embodiment, the signal S1 could be coupled to a network providing a remotely located air evacuation indicator 60, for example, at a nurses' station, or to a local area network allowing access to the signal S1 through the LAN.

Figure 4:
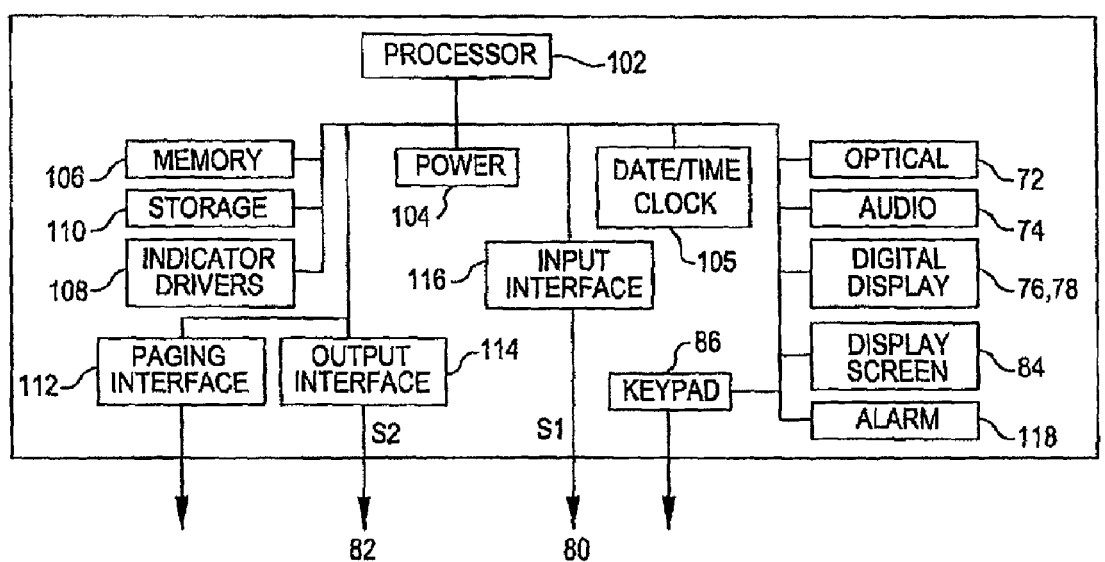
FIG. 4 is a block diagram that illustrates an indicator controller, in accordance with an embodiment of the invention.

Air evacuation indicator 60 includes an indicator controller 100 (not shown), which may be carried by air evacuation indicator 60, and is described in conjunction with FIG. 4. Indicator controller 100 may be removably coupled to the bubble detector 46 and the signal S1 by detector coupler 47, which is connected at signal input jack 80 in the embodiment illustrated. Indicator controller 100 receives the signal S1 and generates an indicator control signal S2 for driving at least one indicator. Indicator control signal S2 is externally provided at external output at jack 82. Air evacuation indicator 60 includes an optical indicator device 72 in the form of indicator light arranged to blink in response to signal S2. Optical indicator device 72 may be a light emitting diode arranged to blink each time a bubble is detected. Audio indicator device 74 may be a speaker arranged to beep each time a bubble is detected. The indicators of air evacuation indicator 60 may be configured to provide an alarm when the air flow exceeds a predetermined level, which in the embodiment illustrated occurs when the number of bubbles exceed a predetermined level. The alarm may be provided by driving the speaker 74 to sound a wailing sound or other sound pattern generally associated with an alarm condition, or may be provided by an alarm indicator (not shown). While air evacuation indicator 60 and bubble detector 46 are shown in separate housings, they may be integrated into a single device carried within the self-contained underwater chest drain unit 30.

In operation, a vacuum created by vacuum source 20 is applied to the self-contained, underwater chest drain unit 30. The vacuum is applied to the patient's chest cavity 51 by underwater chest drain unit 30 through inlet tube 58 and chest drain tube 52. The vacuum evacuates fluid from the patient's chest, including any air from air leaks in the patient, into underwater chest drain unit 30. Any liquid is collected in collection chamber portion 36, and any air evacuated is drawn by the vacuum into bubble chamber 42 at water-seal portion inlet port 48. The vacuum draws any air through bubble chamber fluid 45 and forms bubbles 44 in fluid column 43. Bubble detector 46 detects individual bubbles of bubbles 44 flowing in fluid column 43, and generates signal S1 in response to the number of bubbles detected.

Controller 100 receives signal S1 from bubble detector 46 via detector coupler 47, and generates control signal S2. Typically, signal S2 is suitable for driving the indicator devices. Indicator devices of the type used to implement the aspect of the invention illustrated in FIG. 2 are likely to require more power than is available in signal S1. In addition, signal S1 may not be suitable for controlling the behavior of the indicator device, such as the length of a beep or flash. Control signal S2 is provided to drive the indicator devices each time a bubble is detected, such as optical indicator device 72 and audio indicator device 74. In a preferred embodiment, optical indicator device 72 is an LED that flashes once each time a bubble is detected, and audio indicator device 74 is a speaker that beeps once each time a bubble is detected. The duration of the flash and the beep may be established by signal S2, or by the physical parameters of the indicator device. Air evacuation indicator 60 may include a switch (not shown) allowing indicator selection. For example, the audio indicator device 74 may be turned off while the patient is sleeping, leaving visual indicator device 72 active. This provides an improvement over existing visual bubble monitoring systems requiring a health care provider to observe and count the bubbles 44 moving through fluid column 45, and further provides an alarm not present in existing visual air evacuation indicators. An aspect of the invention also provides an improvement over existing air evacuation indicators because it provides the air flow signal S1, which includes features from which electronic data may be generated concerning air evacuation from the chest cavity.

Chest drain systems occasionally experience air leaks, which may occur for example between the chest tube 52 and the patient's chest cavity 51, or which may occur from a lack of system vacuum integrity. Occasionally, a chest drain system is knocked over causing it to fail to function properly, or a system otherwise fails to function properly and allows ambient air into the vacuum path. System air leaks concern health care providers because they may reduce the vacuum applied to the patient's chest cavity 52, and allow lung 51 to re-collapse. Provision of an alarm-employing audio indicator device 74 is an important advantage over existing devices used to drain a chest cavity.

While certain aspects of the invention are described above with respect to a "wet" or "underwater" system, other embodiments of the invention provide an air evacuation indicator for "dry" or "waterless" chest drain systems. An aspect of the invention includes providing for a bubble chamber 42, a fluid column 45, and a bubble detector 46 in a water-seal portion of a vacuum path of a dry chest drain system. Air evacuation indication is provided in substantially the same manner for dry chest drain systems as described above.

Figure 3:
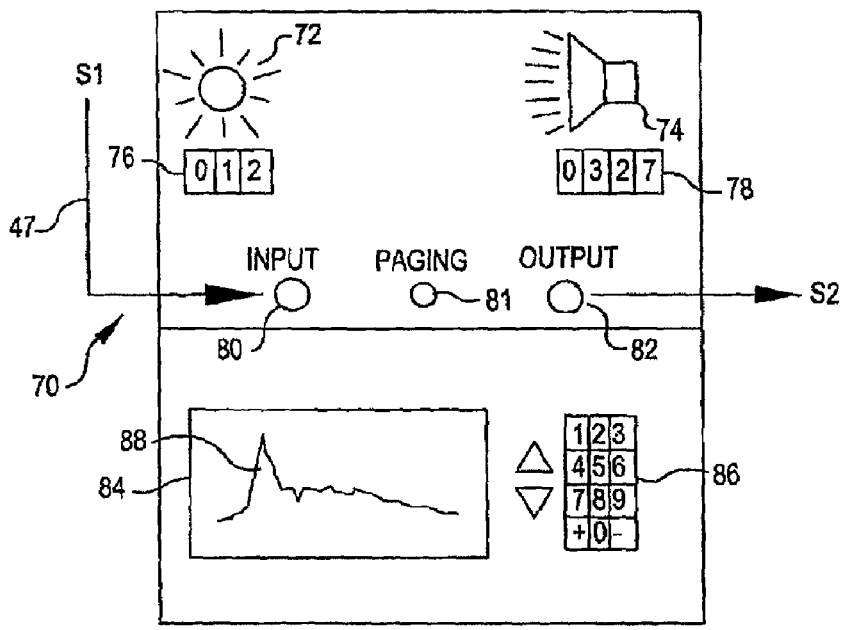
FIG. 3 illustrates indicator devices that provide additional air evacuation indication, in accordance with an embodiment of the invention.

FIG. 3 illustrates an air evacuation indicator device 70 that provides additional air evacuation indication, in accordance with an embodiment of the invention. Indicator device 70 is similar to air evacuation indicator 60, and additionally includes a first digital indicator device 76, a second digital indicator device 78, a display screen 84, and a keypad 86. Indicator device 70 is operated by an indicator controller 100 described in additional detail in conjunction with FIG. 4. First digital indicator 76 provides a plurality of digits for indicating an aspect of an air evacuation, and second digital indicator 78 provides a plurality of digits for indicating another aspect of an air evacuation.

An embodiment of indicator device 70 is illustrated in FIG. 3 where first digital indicator 76 includes three digits, and is configured to display an air evacuation rate in bubbles per minute. Second digital indicator device 78 includes four digits and is configured to display air evacuation during a previous hour, which in this embodiment is in a parameter of bubbles per hour. In an alternative embodiment, a digital indicator may be used to indicate an air evacuation rate on a predetermined scale. For example, a scale from one to ten could be established, where "0" indicates no air being evacuated, "5" indicates an intermediate rate of air evacuation, and "10", indicates an alarming rate of air evacuation. The information displayed on first and second digital indicators 76 and 78 may be configured from a menu displayed on display screen 84 and entries made on keypad 86. Display screen 84 may be configured to display historical air evacuation information 88 in a manner similar to a strip chart, with a horizontal axis for time and a vertical axis for bubbles per unit of time. The historical air evacuation information 88 may assist a provider in determining the patient's and the system's air evacuation history. The information displayed on display screen 84 may be configured from a menu displayed on display screen 84 and entries made on keypad 86. In an alternative embodiment, indicator device 70 may provide a printer for creating a hardcopy of the historical air evacuation information 88.

The indicator controller 100 may be arranged to filter signal S1 to eliminate noise or extraneous features. Such filter could be passive or active, and may involve digitally filtering signal S1.

A computer, such as a laptop, may be used as an air evacuation indicator. A program, such as LABVIEW® by NATIONAL INSTRUMENTS®, Inc., Austin, Tex., may be used to acquire signal S1, or indicator control signal S2 at output jack 82, and display air evacuation indicator information.

FIG. 4 is a block diagram illustrating an indicator controller 100, in accordance with an embodiment of the invention. The indicator controller 100 may be any device known in the art appropriate for receiving the signal S1, discerning its features, and generating an indicator control signal S2 arranged to drive at least one indicator device.

A relatively simple indicator controller 100 is used when the air evacuation information to be indicated is simply blinking optical indicator device 72 and beeping audio indicator device 74 once for each bubble. A more robust indicator controller 100 is used when the air evacuation information to be indicated includes breathing rate and vacuum pressure applied to the chest cavity 51, or includes historical information. A robust indicator controller 100 may include microprocessor or microcontroller functionality to store data, compute rates, and generate a signal to drive the indicator devices. FIG. 4 illustrates an indicator controller 100 that includes microprocessor or microcontroller functionality for providing air evacuation information. Indicator controller 100 is arranged to receive the signal S1 and generate control signal S2 to operate air evacuation indicators as described in conjunction with FIGS. 2 and 3. Indicator controller 100 may include more or less components than those shown in FIG. 4, depending on the information to be provided by the air evacuation indicator. As shown in the figure, indicator controller 100 includes processor unit 102, power 104, clock 105, memory 106, indicator drivers 108, storage 110, paging interface 112, output interface 114, and input interface 116. Optical indicator 72, audio indicator 74, digital displays 76 and 78, display screen 84, keypad 86, and alarm 118, are included for clarity in illustrating indicator controller 100.

Mass memory includes memory 106 and storage 112, and generally includes RAM, ROM, and one or more data storage units. The indicator drivers 108 may be devices having circuitry that is responsive to signal S2 and configured to operate the indicator devices 72, 74, 76, 78, 84, and 118. Alternatively, the indicator drivers 108 may be software-based drivers configured to include driver information in signal S2 to operate the indicator devices 72, 74, 76, 78, 84, and 118. Software-based indicator drivers 108 may be stored in memory 106 or storage 112, or stored in a separate device. Any instructions to be executed by processor 102 may be stored in the mass memory.

Indicator controller 100 includes an output interface 114 for communicating with external devices, and provides indicator control signal S2 at output jack 82. Indicator controller 100 also includes power supply 104 powering indicator controller 100, the several indicator devices, and the bubble detector 47. A rechargeable or non-rechargeable battery may be used to provide power. The power may also be provided by an external power source, such as common AC, or an AC adapter. Keypad 86 may be any input device arranged to receive input from a user. For example, keypad 86 may include a push-button numeric dial, scrolling keys, and/or a keyboard. Keypad 86 may also include command buttons that are associated with selecting and displaying air evacuation indicator information.

Display screen 84 may be a liquid crystal display (LCD), gas plasma, light emitting diode (LED), or any other type of display used with a portable device. Display screen 84 may also include a touch-sensitive screen arranged to receive input from an object such as a stylus or a digit from a human hand Alarm 118 may be an audio optical device that provides a sound associated with an urgent or emergency situation. Alternatively, the alarm sound may be provided by driving audio indicator device 74 in a manner to provide an alarm sound. Clock 105 provides date/time information for tracking when a bubble is counted for air evacuation rate indication.

In operation, input interface 116 receives the signal S1 from signal input terminal 82. Processor unit 102 generates indicator control signal S2 with appropriate driver information from indicator drivers 108 to drive the indicator devices 72, 74, 76, 78, 84, and 118. Features of signal S1 may be stored in mass memory. The stored features may be used for generation of air evacuation history indication and/or air evacuation rate indication. Signals S1 and S2, and stored features may be downloaded from output port 82 via output interface 114. Paging information may be sent by paging interface 112 to a remote location when a preselected condition occurs, such as an alarm condition.

Figure 5:
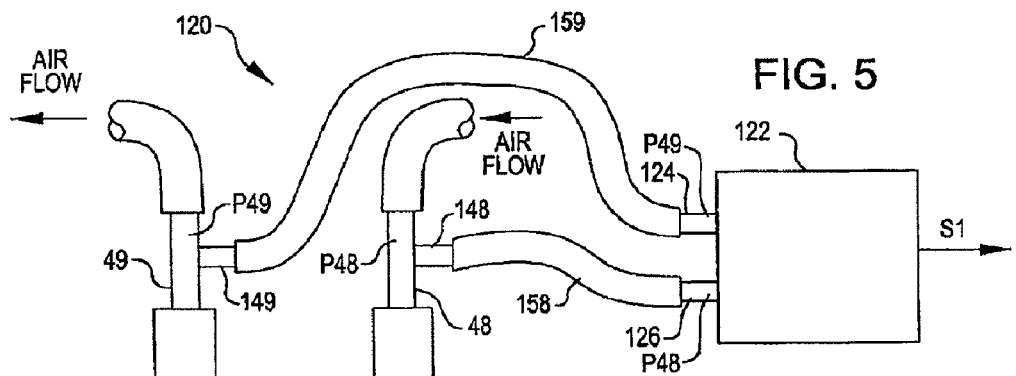
FIG. 5 illustrates an assembly for providing information related to air evacuation that includes an air escapement conduit in the form of a water-seal chamber, and a differential pressure transducer, according to an embodiment of the invention.

FIG. 5 illustrates an assembly for providing information related to air evacuation that includes an air escapement conduit in the form of a water-seal chamber 120, and a differential pressure transducer 122, according to an embodiment of the invention. Water-seal chamber 120 is substantially similar to water-seal chamber 40. Water-seal chamber 120 additionally includes a pressure measuring port 38 coupled to inlet port 148 for measuring inlet pressure $P_{48}$, and a pressure measuring port 39 coupled to outlet port 149 for measuring outlet pressure $P_{49}$. Like water-seal chamber 40, water-seal chamber 120 may be used with a wet manometer chamber 32 or a dry vacuum configuration (not shown).

Differential pressure transducer 122 includes inlet ports 124 and 126 for receiving pressures $P_{48}$ and $P_{49}$, respectively, and an output for the signal S1. Differential pressure transducer 122 may be any differential pressure transducer, sensor, or other device known in the art suitable for measuring a pressure differential between the inlet pressure $P_{48}$ and the outlet pressure $P_{49}$, and generating the air flow signal S1 in response. As described below, an aspect of the $P_{48}$-$P_{49}$ pressure differential is a transitory pressure differential caused by the escapement of air through the water-seal chamber 120. In addition to measuring a pressure differential, the pressure sensor transducer 122 may also be arranged to measure the pressures $P_{48}$ and $P_{49}$, the ambient air pressure $P_{Amb}$, and provide the measurements as additional features of signal S1. The inlet ports 124 and 126 of differential pressure transducer 122 are coupled by hoses 158 and 159 to the respective inlet ports 148 and 149 of water-seal chamber 120. In an alternative embodiment, the differential pressure transducer 122 may include pressure sensors directly coupled to inlet port 148 and outlet port 149, and the pressure sensors are electrically coupled to differential pressure transducer 122.

The parameters of the air flow between inlet port 148 and outlet port 149 include velocity, volume, and pressure drop, any one of which may be measured to provide features to the signal S1 related to the air flow. The pressure drop results from the resistance to air flow presented by the fluid 45 in the fluid column 43. The bubbles 44 flowing through the water-seal chamber 120 are formed in response to the pressure differential $P_{48}$-$P_{49}$. Evacuated air flows into the inlet port 48, and is drawn by the $P_{48}$-$P_{49}$ pressure differential through the fluid 45 in fluid column 43. A bubble 44 is formed in the fluid 45, rises to the surface of the fluid 45 in the outlet port 49 side of the fluid column 43, and bursts. The air formerly contained in the bubble 44 flows out the outlet port 49. As this air flow occurs, a transitory $P_{48}$-$P_{49}$ pressure differential $P_{TPD}$ is created between inlet port 48 and outlet port 49 that correlates to the escapement and bursting of the bubble 44.

In operation, differential pressure transducer 122 detects the pressure differential $P_{TPD}$, and responds by providing a feature of signal S1 related thereto. The differential pressure transducer 122 may also be used to sense additional air evacuation information. For example, the inlet pressure $P_{48}$ varies slowly over time with the patient's breathing, sometimes called tidaling. This causes the $P_{48}$-$P_{49}$ pressure differential to also vary slowly, which may be a feature included in the signal S1. The absence of tidaling may be indicated by indicator device 70 as a situation where the chest drain tube 52 is plugged.

As a further example, when arranged to measure ambient air pressure $P_{Amb}$, the differential pressure transducer 122 can include the $P_{Amb}$ as a feature in signal S1. Processor 102 may be arranged to compare $P_{Amb}$ and the inlet pressure $P_{48}$ to determine the level of vacuum ($P_{Amb}$-$P_{48}$) being applied to chest cavity 51. When the vacuum level is below a preselected value, a leak may be present in the chest drain tube 52, or between the tube 52 and the chest cavity 51. When the vacuum level is above another preselected value, an obstruction may be present in the chest drain tube 52, such as a kink or blockage, or between the tube 52 and the chest cavity 51.

Air evacuation indicator 70 may be further arranged to provide an alarm or notification of a low and/or high vacuum situation.

By way of further description, operation of water-seal chambers 40 and 120 is contrasted. An aspect of the invention illustrated in FIG. 2 employs a bubble detector 46 to individually count the bubbles 44 formed in the escapement mechanism presented to the evacuation air flow, in the form of the water-seal chamber 40. The detector 46 provides a signal S1 responsive to each counted or detected bubble 44. The indicator device 70 receives the signal S1, and in response may represent or indicate the volume of air evacuated in bubbles. Alternatively, bubbles could be converted by the indicator device 70 into a unit of air volume, or some other parameter. Another aspect of the invention illustrated in FIG. 5 employs a water-seal chamber 120 and a differential pressure transducer 122. This aspect senses or detects the transitory $P_{48}$-$P_{49}$ pressure differential $P_{TPD}$ across the chamber 120 representing evacuation air flow, the air flow being quantified in bubbles 44 formed in the escapement mechanism presented to the evacuation air flow, in the form of the water-seal chamber 120. The pressure $P_{TPD}$ event occurs as a bubble 44 passes through water-seal chamber 120. The differential pressure transducer 122 provides a signal S1 responsive to each pressure $P_{TPD}$ event. While the event may be correlated to a bubble 44, the aspect of the invention illustrated in FIG. 5 does not count bubbles as such. The signal S1 provided by the water-seal chamber 120 and differential pressure transducer 122 may include features not obtainable with water-seal chamber 40 and bubble detector 46. As with the chamber 40, the indicator device 70 receives the signal S1 and may represent or indicate the volume of air evacuated in bubbles, or alternatively be arranged to represent air evacuation levels or units of air volume.

Figure 6:
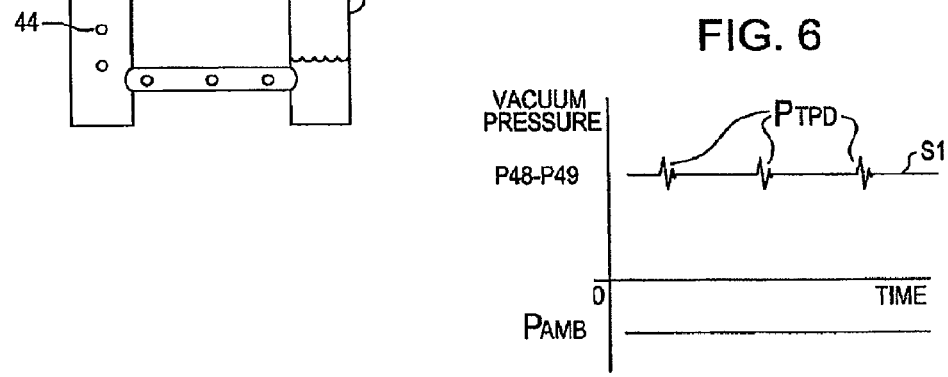
FIG. 6 illustrates a signal S1 produced by the differential pressure transducer of FIG. 5, in accordance with the invention.

FIG. 6 illustrates a signal S1 produced by the differential pressure transducer 122 of FIG. 5, in accordance with the invention. A horizontal axis represents time and a vertical axis represents vacuum pressure. Each $P_{TPD}$ event will produce a transient signal feature of signal S1 as illustrated. The average value of the $P_{48}$-$P_{49}$ pressure differential will slowly vary with the patient's breathing (tidaling), and will produce a slow variation in the average $P_{48}$-$P_{49}$ pressure differential feature of signal S1 corresponding to the patient's breathing rate. Furthermore, the differential pressure transducer 122 may also produce a feature of signal S1 that includes the ambient pressure $P_{Amb}$.

Figure 7:
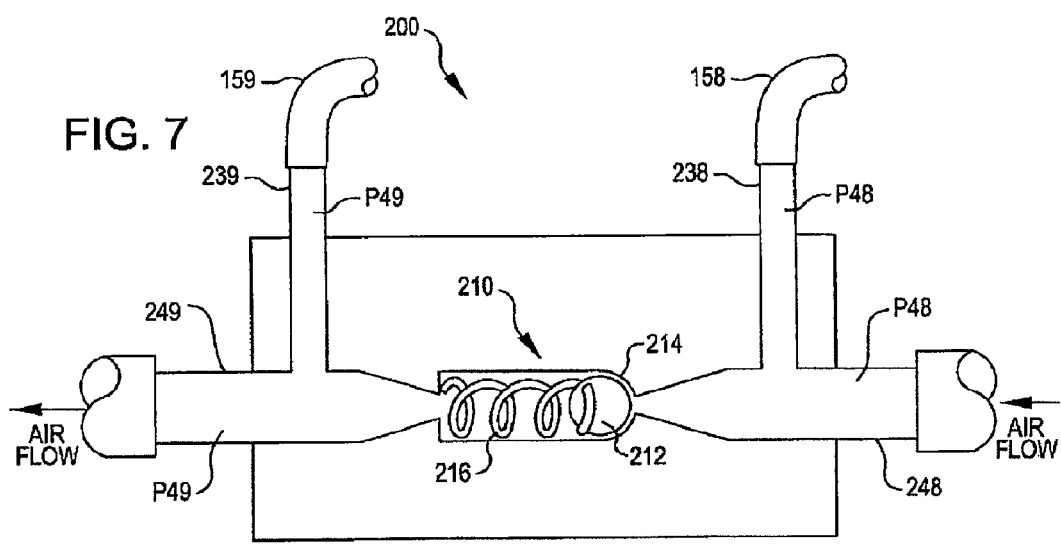
FIG. 7 illustrates an air escapement conduit that includes a one-way valve and measuring ports for measuring air pressure across the one-way valve, according to an embodiment of the invention.

FIG. 7 illustrates an air escapement conduit 200 that includes a one-way valve 210 and measuring ports 238 and 239 for measuring air pressure across the one-way valve, according to an embodiment of the invention. The air escapement conduit 200 includes an inlet port 248 having a $P_{48}$ measuring port 238 in fluid communication with it, an outlet port 249 having a $P_{49}$ measuring port 239 in fluid communication with it, and the one-way valve 210.

Inlet port 248 is arranged to receive and outlet port 249 is arranged to discharge evacuation air flow from the chest cavity 51 in substantially the same manner as ports 48 and 49 of FIG. 2. Measuring ports 238 and 239 are arranged for measuring inlet pressure $P_{48}$ and outlet pressure $P_{49}$ respectively by the differential pressure transducer 122 in substantially the same manner as ports 148 and 149 of FIG. 6.

The one-way valve is illustrated as a ball valve 210 that includes a ball 212, a seat 214, and a bias member illustrated as a coiled spring 216. The ball 212 is sealingly biased against the seat 214 with a selected bias provided by coiled spring 216. The ball valve 210 forms an escapement mechanism that allows the evacuation air flow from the chest cavity 51 in discrete measurable units, the size of which depend on the physical parameters of the ball valve 210 and the $P_{48}$-$P_{49}$ pressure differential. The ball valve 210 may allow air flow when the patient is exhaling as illustrated, and seals against air entering the chest cavity 51 when the patient inhales, both in a manner substantially similar to the water-seal chambers 40 and 120. The bias of coiled spring 216 is selected to control the escapement by providing an appropriate $P_{48}$-$P_{49}$ pressure differential, both for measuring each $P_{TPD}$ event by the transducer 122, and for providing an appropriate vacuum level to the chest cavity 51. For example, the bias of coiled spring 216 may be selected to provide between 2 and 4 cm $H_2O$ of bias pressure against the air flow. In an alternative embodiment, the one-way valve 120 may be any device that allows evacuation air flow, allows a suitable vacuum level to be applied to the chest cavity 51, obstructs inhalation air flow, and provides a measurable air pressure drop during evacuation air flow. For example, the one-way valve may be a piston and seat combination, or a flapper valve that is biased closed with a predetermined force.

In operation, the outlet port 249 is coupled to a vacuum source having an appropriate level of vacuum for the patient 50, for example between −10 and −40 cm $H_2O$. The vacuum source may be from a dry system or a wet system, the dry system being preferable because the noise generated by the wet system requires additional filtering of signal S1. The inlet port 248 is coupled to the collection chamber 36, which is in turn coupled to the chest drain tube 52 and the chest cavity 51. For example, if the vacuum pressure $P_{49}$ at outlet port 249 is −20 cm $H_2O$, and if the coiled spring 216 one-way valve 210 provides a bias of +2 cm $H_2O$, the vacuum pressure $P_{48}$ at inlet port 248 will be −18 cm $H_2O$. The inlet ports 124 and 126 of differential pressure transducer 122 are coupled by hoses 158 and 159 to the respective inlet ports 238 and 239 of air escapement conduit 200. Once an initial evacuation is completed, the chest cavity 51 will have a vacuum applied to it of about −18 cm $H_2O$, and one-way valve 210 will be biased closed by spring 216. An air leak into the chest cavity 51 will reduce the vacuum in the chest cavity and the vacuum pressure $P_{48}$ at inlet port 248 below −18 cm $H_2O$. A transitory pressure differential event $P_{TPD}$ will occur. The +2 cm $H_2O$ bias of spring 216 will be overcome, the one-way valve 210 will open, air will be evacuated from the chest cavity 51 until equilibrium is achieved, the one-way valve 210 will close, and the vacuum applied to the chest cavity 51 returns to −18 cm $H_2O$. The differential pressure transducer 122 will provide a signal S1 from the air escapement conduit 200 in substantially the same manner and with substantially the same features as described in conjunction with FIGS. 5 and 6.

Alternative embodiments of the air escapement conduit 200 may be used to create the transitory pressure differential event $P_{TPD}$. For example, the air escapement conduit 200 may be arranged to include a detector that senses the opening and closing movements of the one-way valve 210 allowing evacuation air flow, and generate the signal S1. By way of further example, the one-way valve 210 may be configured such that a mechanical shock or vibration is created when the ball 212 closes and opens with respect to the seat 214. An electroacoustic transducer such as a microphone may be used to respond to the mechanical shock or vibration and create the signal S1. In such an alternative embodiment, the ports 238 and 239 may be eliminated if additional signal S1 features are not desired.

Although the present invention has been described in considerable detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. An air evacuation indicator device for providing information about air evacuation from a chest cavity, the device comprising: an air escapement conduit having an inlet port providing air communication with the chest cavity and an outlet port providing air communication with a vacuum source, the conduit allowing an air flow from the inlet port to the outlet port in response to a pressure differential between the inlet and outlet ports; and a detector responsive to the air flow that provides a signal related to the air flow;

wherein the air escapement conduit includes a bubble chamber having a fluid disposed between the inlet port and the outlet port, the bubble chamber arranged so that air flowing between the inlet port and the outlet port flows through the fluid and forms bubbles.

2. The air evacuation indicator device of claim 1, further comprising an indicator device operable to provide evacuation information in response to the signal.

3. The air evacuation indicator device of claim 2, wherein the indicator device includes an optical indicator element.

4. The air evacuation indicator device of claim 3, wherein the optical indicator element includes a light emitting diode.

5. The air evacuation indicator device of claim 2, wherein the indicator device includes an audio element.

6. The air evacuation indicator device of claim 2, wherein the indicator device includes a digital indicator device.

7. The air evacuation indicator device of claim 2, further including a storage device arranged to store data representative of the signal.

8. The air evacuation indicator device of claim 1, wherein the air escapement conduit includes a mechanical valving mechanism.

9. The air evacuation indicator device of claim 1, wherein the detector is a pressure differential sensor operable to detect a difference in air pressure between the inlet port and the outlet port, and to generate a signal related to the difference.

10. The air evacuation indicator device of claim 1, wherein the detector is an air pressure detector responsive to air pressures at the inlet and outlet ports, and that provides a signal having features related to the air pressures.

11. The air evacuation indicator device of claim 10, wherein the air pressure detector is further responsive to ambient air pressure and that provides a signal having features related to the ambient air pressure.

12. The air evacuation indicator device of claim 1 wherein the indicator device is further operable to correlate time of occurrence with signal features.

13. The air evacuation indicator device of claim 1, wherein the indicator device is further operable to discriminate features of the signal to produce separate corresponding indications.

14. The air evacuation indicator device of claim 1, wherein the indicator device is further operable to provide an alarm when a volume of air evacuated in a selected unit of time exceeds a predetermined level.

15. The air evacuation indicator device of claim 1, wherein the evacuation information includes air volume evacuated from the chest cavity.

16. The air evacuation indicator device of claim 1, wherein the evacuation information includes rate of air volume evacuation from the chest cavity.

17. The air evacuation indicator device of claim 1, wherein the evacuation information includes air volume evacuated per selected unit of time over time.

18. The air evacuation indicator device of claim 1, wherein the evacuation information includes respiration rate of the chest cavity.

19. The air evacuation indicator device of claim 1, wherein the evacuation information includes negative air evacuation pressure applied to the chest cavity.

* * * * *

UNITED STATES PATENT AND TRADEMARK OFFICE
CERTIFICATE OF CORRECTION

| | | |
|---|---|---|
| PATENT NO. | : 7,798,974 B2 | Page 1 of 1 |
| APPLICATION NO. | : 11/738412 | |
| DATED | : September 21, 2010 | |
| INVENTOR(S) | : Sirokman | |

It is certified that error appears in the above-identified patent and that said Letters Patent is hereby corrected as shown below:

Title Page;
On Page 2 (Item 56), Column 1, Line 13, under Other Publications, change "Certamics" to --Ceramics--.

On Page 2 (Item 56), Column 2, Line 5, under Other Publications, change "Thorascostomy;" to --Thoracostomy;--.

In Column 1, Line 10, after "2002" insert --.--.

In Column 1, Line 59, after "fatal" insert --.--.

In Column 8, Line 42, change "nurses'station," to --nurses' station,--.

In Column 10, Line 24, change ""10"," to --"10"--.

In Column 11, Line 43, after "hand" insert --.--.

Signed and Sealed this
Fifteenth Day of March, 2011

David J. Kappos
*Director of the United States Patent and Trademark Office*